(12) United States Patent
Krebs

(10) Patent No.: US 6,962,154 B2
(45) Date of Patent: Nov. 8, 2005

(54) METERED ADMINISTRATION OF A THERAPEUTIC GAS

(75) Inventor: Christian Krebs, Vosendorf (AT)

(73) Assignee: INO Therapeutics GmbH, (AT)

(*) Notice: Subject to any disclaimer, the term of this patent is extended or adjusted under 35 U.S.C. 154(b) by 0 days.

(21) Appl. No.: 10/780,161

(22) Filed: Feb. 17, 2004

(65) Prior Publication Data
US 2004/0168686 A1    Sep. 2, 2004

(30) Foreign Application Priority Data
Feb. 18, 2003 (DE) .................. 103 06 766

(51) Int. Cl.⁷ .................................. A61M 15/00
(52) U.S. Cl. .................. 128/203.12; 128/203.14; 128/202.22; 128/203.25
(58) Field of Search .............. 128/202.22, 203.12, 128/203.14, 204.22, 204.23, 205.23, 203.25

(56) References Cited

U.S. PATENT DOCUMENTS

| | | | |
|---|---|---|---|
| 4,270,564 A * | 6/1981 | Blackburn et al. | 137/240 |
| 4,459,266 A * | 7/1984 | Lamoreaux | 422/86 |
| 4,617,924 A * | 10/1986 | Heim et al. | 128/204.23 |
| 4,633,859 A * | 1/1987 | Reneau | 128/205.26 |
| 5,398,675 A * | 3/1995 | Henkin et al. | 128/203.12 |
| 5,507,280 A * | 4/1996 | Henkin et al. | 128/203.12 |
| 5,531,218 A * | 7/1996 | Krebs | 128/203.12 |
| 5,558,083 A * | 9/1996 | Bathe et al. | 128/203.12 |
| 5,687,709 A * | 11/1997 | Akerberg | 128/203.12 |
| 6,021,777 A * | 2/2000 | Post et al. | 128/204.13 |
| 6,032,667 A * | 3/2000 | Heinonen | 128/205.24 |
| 6,142,147 A * | 11/2000 | Head et al. | 128/204.21 |
| 6,258,341 B1 * | 7/2001 | Foster et al. | 424/45 |
| 6,474,333 B1 * | 11/2002 | Heinonen | 128/203.12 |
| 6,581,599 B1 * | 6/2003 | Stenzler | 128/204.23 |
| 6,668,828 B1 * | 12/2003 | Figley et al. | 128/204.18 |
| 6,718,980 B2 * | 4/2004 | Carter | 128/205.24 |
| 6,786,217 B2 * | 9/2004 | Stenzler | 128/204.23 |

FOREIGN PATENT DOCUMENTS

EP          0 861 672 A1    9/1996

* cited by examiner

Primary Examiner—Aaron J. Lewis

(57) ABSTRACT

The invention relates to a method for the metered administration of a therapeutically effective gas to a patient, comprising a step to remove harmful or undesired substances from the gas-carrying system or from parts of the gas-carrying system. According to the invention, the step consists of purging with one or more other gases or gas mixtures and/or it consists of evacuation.

15 Claims, 7 Drawing Sheets

METERED ADMINISTRATION OF A THERAPEUTIC GAS

FIELD OF INVENTION

The invention relates to a method and to a device for the metered administration of a therapeutically effective gas to a patient, comprising a purging step for purposes of removing harmful substances from parts of the gas-carrying system.

BACKGROUND OF INVENTION

Nowadays, nitric oxide, NO, has become known as a medication against pulmonary hypertension, in other words, as a vasodilator. The advantage of treatment with the widely described NO mixtures is that NO only acts locally, that is to say, in the pulmonary circulation system, and not systemically. The NO gas mixture is administered to patients through inhalation. This means that other gas components, especially air, oxygen or other gases containing oxygen, are admixed to the therapeutically effective gas by means of various techniques.

For ventilated patients, European patent application EP 621 051 A2 discloses the procedure of metering in the nitrogen oxide mixture so that it is proportional to the volumetric flow rate, in other words, as a function of the inspiratory, inhaled flow of the air-oxygen mixture. The flow of the NO mixture can also be metered in so that it corresponds to the inhaled volume.

U.S. Pat. No. 5,839,433 or world patent WO 98/31282 discloses additional techniques for the administration of NO to a patient. These publications describe the so-called spike, peak or pulse techniques. For this purpose, a valve is usually opened for a certain period of time and then closed again during the inspiratory phase in order to dispense a certain volume of NO to the lungs of the patient. This technique is normally—although not exclusively—employed for spontaneously breathing patients, that is to say, for patients who are not hooked up to a ventilator.

Irrespective of which method is chosen for the dosing of NO, there is always a negative side effect associated with NO treatment, namely, the fact that NO is converted into $NO_2$ over the course of time when NO is mixed together with a gas that contains oxygen. Since air consists of approximately 21% oxygen, this phenomenon also occurs in air. If more time passes during which NO is present in the air or in oxygen, then more $NO_2$ is formed. For instance, more $NO_2$ is generated when the NO therapy is started, interrupted or resumed—since there is more time for oxidation. In other words, this is the case whenever time is available for further oxidation and whenever air and NO are present in the feed tubes and in the areas between the individual devices or else in the patient connector, which can be, for instance, a nosepiece or a mask. During such pauses, there is usually still NO in the lines and it can then react to form $NO_2$. Then, as a rule, the gas present in the system contains a relatively large amount of $NO_2$ which either has to be purged or else it reaches the patient. Since harmful effects already occur at minute concentrations, even the smallest amounts of $NO_2$ should not be tolerated. This problem occurs particularly often—although not exclusively—in the case of spontaneously breathing patients whereby, for example, nosepieces or masks that do not fit well fail to trigger the desired action, namely, the dosing of NO mixtures. As a result, the mixture remains in the feed line and then reacts in the presence of oxygen to form $NO_2$. But also due to some other erroneous detection by the sensor which triggers the start of the inspiration and thus the NO pulse to the patient, or else due to other events that prevent the initiation of the next gas mixture pulse or pulses, the NO mixture present in the feed line together with air/oxygen can lead to an elevated formation of $NO_2$. As a result, after a renewed triggering, the patient receives gas that has an elevated content of $NO_2$.

In order to eliminate this drawback, U.S. Pat. Nos. 6,125,846 and U.S. Pat. No. 6,109,260 each disclose a device and a method comprising a purging process. This purging process is done in such a way that, whenever there is a prolonged pause in the administration or else an apnea pause, the $NO_2$ mixture is purged by a prolonged continuous volumetric flow of the treatment gas, namely, NO, in order to purge the $NO_2$ mixture. A disadvantage of this approach is that the purging gas itself contains NO so that it can once again react to form $NO_2$ during the next pause. In the worse-case scenario, the patient then once again inhales $NO_2$.

SUMMARY OF INVENTION

Consequently, it is the objective of the invention to improve these methods in such a way that they become safer and the patient is more reliably protected against inhaling $NO_2$ or other harmful gases.

This objective is achieved according to the invention by means of a method that involves a purging step with another gas and/or an evacuation step.

According to a first embodiment of the invention, the gas having the elevated $NO_2$ concentration is not purged out of the system by means of the therapeutic gas containing NO but rather with another gas, especially air, oxygen, nitrogen or other noble gases or mixtures—all of these gases are administered to the patient or else used exclusively for purging purposes. The purging process is the same as that of the state of the art cited, but the purging media are different. Other therapeutically effective gases can also be employed for the purging.

According to a second, independent embodiment of the invention, the gas mixture contaminated with the harmful gas is evacuated from the system by means of a pump so that it can no longer reach the patient.

The therapeutically effective gas is, for instance, NO. The mechanism by which it reacts to form $NO_2$ when it comes into contact with oxygen was already described above. CO constitutes another therapeutically effective gas. This gas can likewise accumulate in the lines during the dosing, as a result of which it might be administered to the patient in undesired high concentrations. Consequently, in the therapy with CO, such a purging step with another gas or an evacuation step can also be advantageous. Examples of other therapeutically effective gases are $CO_2$ mixtures used to stimulate breathing, $H_2$ mixtures, $N_2O$ mixtures, $SF_6$ mixtures, nitrosoethanol, anesthetic gases (such as, for instance, isoflurane and other volatile anesthetic gases, xenon) in order, for example, to terminate the patient's anesthesia.

Therefore, if one of the cases described occurs (sensor no longer detects breathing and does not dispense the dose, a longer interruption of the NO administration starts or ends, or else an NO monitor indicates an elevated $NO_2$ content), the mixture with elevated $NO_2$ is completely purged out of the system all the way to the patient, in other words, from the gas tank to the nosepiece, if possible. The gas elements inside the devices such as tubes and valves should also be freed of $NO_2$ or of the other harmful gas to the greatest extent possible. All dead spaces, feed lines or valves should be purged.

To the greatest extent possible, the evacuation should encompass all of the line parts that come into contact with the gas (nosepiece, mask, tubing, valves, tube lines, sensors, dead spaces).

The purging or evacuation can be time-controlled, sensor-controlled or event-controlled (for instance, the event that the feed of therapeutic gas to the patient is switched off—that is to say, discontinuation of the dosing). Time-controlled means that the purging or evacuation step is carried out for a certain, preset period of time and/or according to a certain time sequence. Sensor-controlled means that the purging or evacuation step is carried out as a function of a measured concentration and/or a measured throughput rate and/or a measured pressure. Particularly during the evacuation, it is recommended that the evacuation be performed to a desired residual pressure in order to ensure that most of the harmful gas is removed.

BRIEF DESCRIPTION OF DRAWINGS

Twelve embodiments of the invention will be explained in greater detail with reference to 14 Figures.

The following is shown.

DETAILED DESCRIPTION

Figure 1:
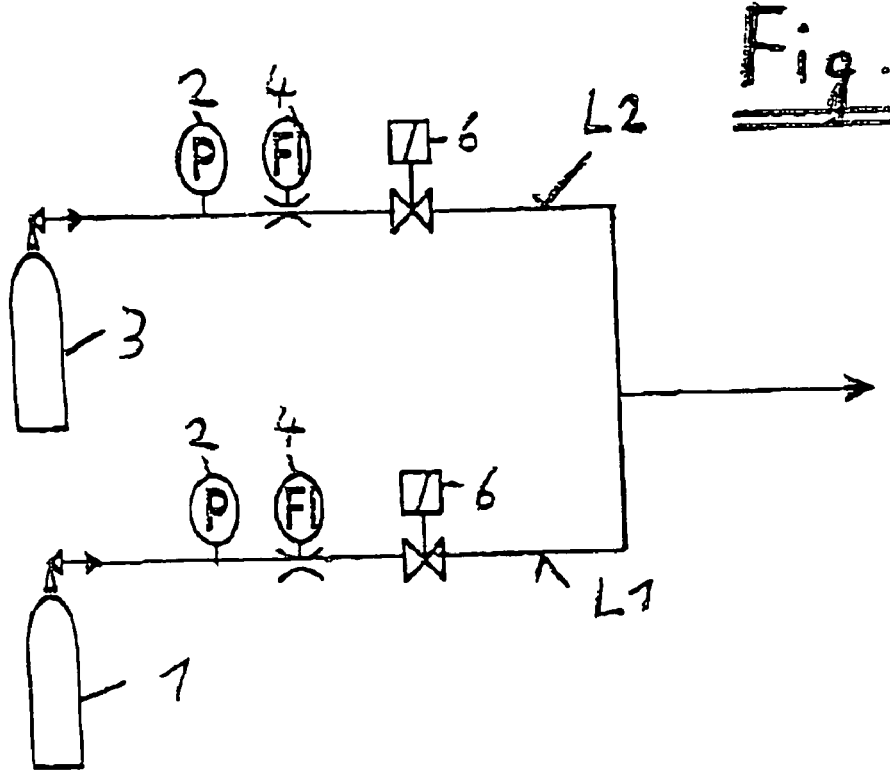
FIGS. 1 to 6 and 13: each depicting a device to carry out a purging operation according to the invention.

FIG. 1 shows a conventional first gas line L1, leading from a first gas tank 1 containing a therapeutic gas, for instance, NO (usually dissolved in nitrogen), to a patient (arrow). The line L1 is fitted with a pressure gauge 2, a flowmeter 4 and a valve 6 for purposes of regulating and controlling the throughput rate. L1 can also be configured without a pressure gauge or flowmeter, or these elements can also be installed at different places, for example, downstream from the control or regulating valve. According to the invention, a second gas line L2 is provided by means of which another gas, namely, the purging gas—here in the example oxygen from the purging gas tank 3—can be flushed through the lines all the way to the patient. This line L2 is likewise fitted with a pressure gauge 2, a flowmeter 4 and a valve 6, this time for the oxygen. The joining of L1 and L2 is only to be understood by way of an example and not as a requirement.

The function of the device according to the invention is as follows: only line L1 is needed in order to treat a patient with NO. It is through this line that pulse-controlled, sensor-controlled, volume-controlled, volumetric flow rate-controlled or time-controlled NO is administered to the patient in the desired dose or quantity. If a pause in the treatment occurs, or in another event due to which the $NO_2$ content in the line rises, a purging step can be carried out by closing the NO valve 6 of line L1 and opening the $O_2$ valve 6 of line L2. in this manner, $O_2$ is flushed through the lines all the way to the patient, thus purging the gas containing $NO_2$ or NO that is present in the lines.

Figure 2:
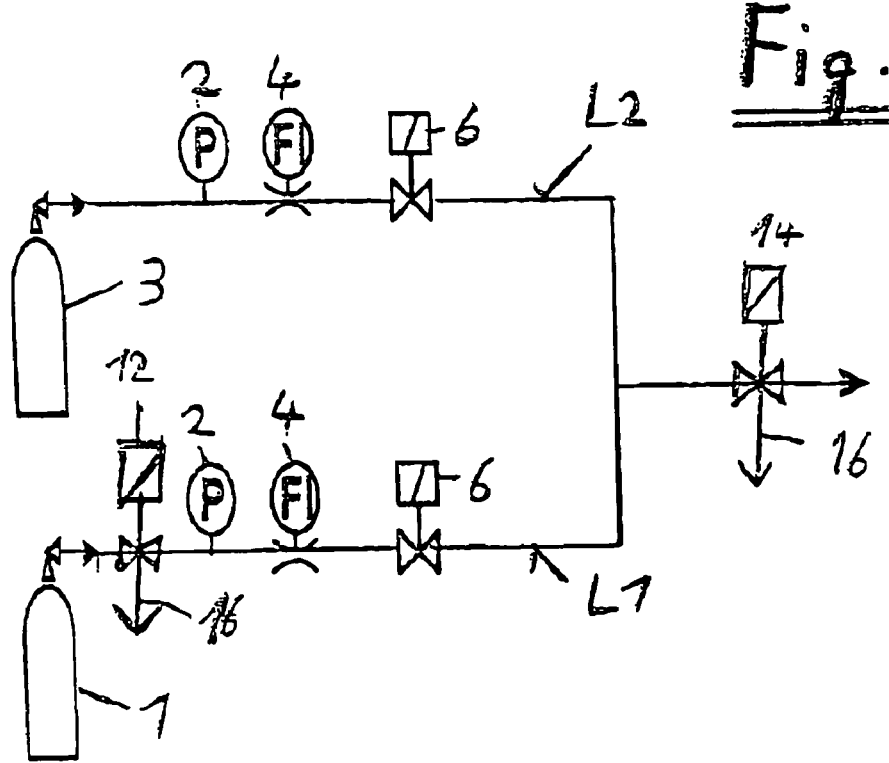

FIG. 2 shows another embodiment of the invention in which the same parts as FIG. 1 are given the same reference numerals. The difference here is that now, near the therapeutic gas tank 1, there is a shut-off valve 12 that additionally has a line 16 leading to the outside. Likewise in FIG. 2, a second shut-off valve 14 is provided which likewise has a line 16 leading to the outside. Possible versions of FIG. 2 are those with either only valve 12 or only with valve 14 or else with both valves. The shared feature in these two configurations is that the valve 12 or the valve 14 can each open a line 16 leading towards the outside atmosphere. In this manner, it is possible to purge directly to the tank 1. The valve 12, for example, for the purging step, can be switched in such a way that it is closed with respect to the therapeutic gas tank 1 and open with respect to line 16. The gas coming from the purging line L2 then flows through line L1 all the way to the valve 12 and from there to the outside. If the valve 14 is also provided, then the purging gas can go from there all the way to the patient or else it can be carried through line 16 to the outside before reaching the patient. In this manner, undesired gas mixtures can already be purged before reaching the patient, and it is also possible to switch between the patient and the outside.

Figure 3:
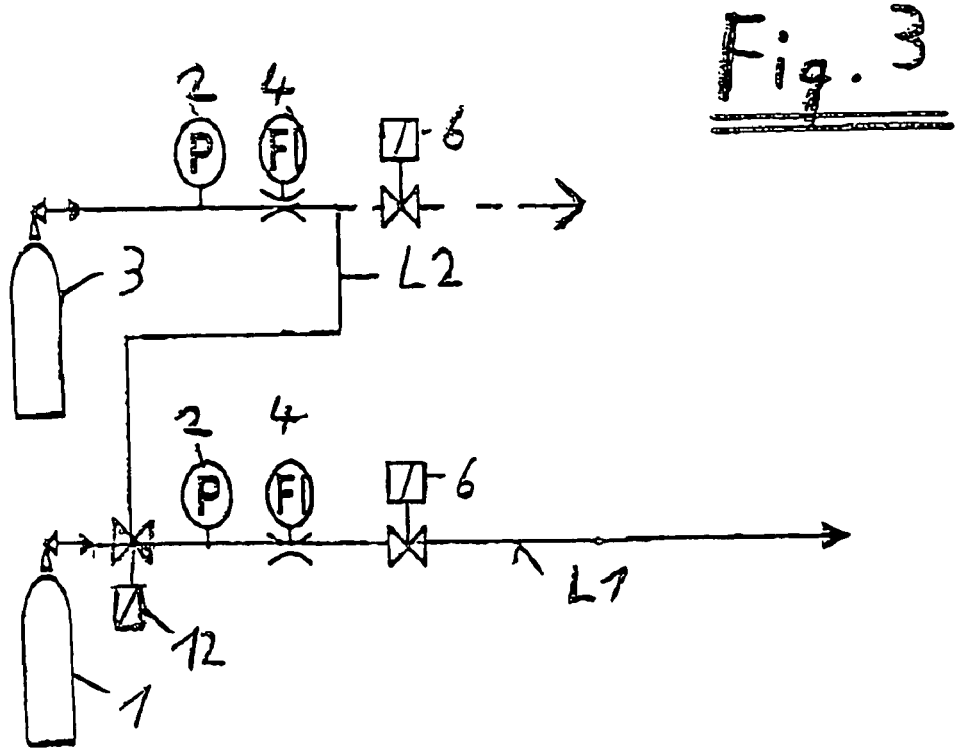

FIG. 3 shows another embodiment in which the purging line L2 is arranged directly before the therapeutic gas tank 1, namely, at the valve 12. Optionally—and consequently indicated by a broken line—a second line can be provided with a valve 6 leading to the patient (arrow). Via this line, the patient can be supplied with a second therapeutic gas from the tank 3. This can be any desired therapeutic gas that brings about an effect that differs from that of the other therapeutic gas. It can also be useful to administer a gas containing oxygen, such as $O_2$ in the tank 3, or such as air or another mixture containing oxygen. This gas can then be employed to ventilate the patient and, in a second step, for purging purposes. In order to treat the patient with the first therapeutic gas, the valve 12 is switched in such a way that the first therapeutic gas is carried from the gas tank 1 all the way to the patient (arrow). For purging purposes, the valve 12 is switched in such a way that the tank 1 is switched off. Then the purging of the entire line L2 and of the line L1 all the way to the patient is initiated.

Figure 4:
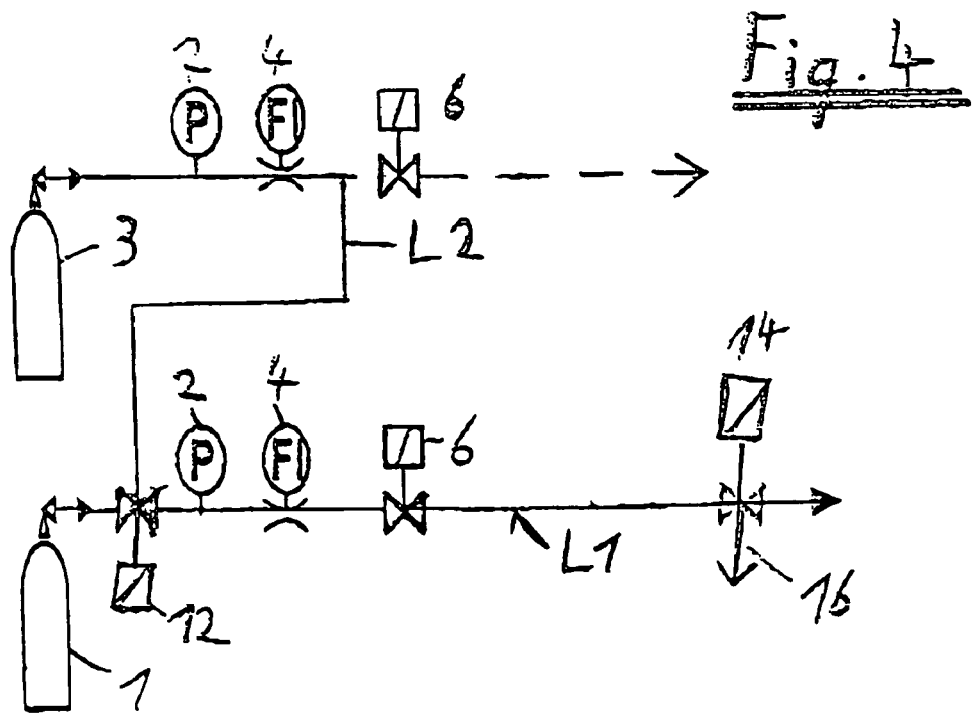

FIG. 4 shows another embodiment whereby here, in comparison to FIG. 3, the valve 14 is additionally provided near the patient connection, said valve having a line 16 leading towards the outside. By means of this valve 14, the line 16 leading to the outside can be purged. Once again, the valve 6 with the optional second line to the patient for the second therapeutic gas from the tank 3 is drawn with a broken line.

Figure 5:
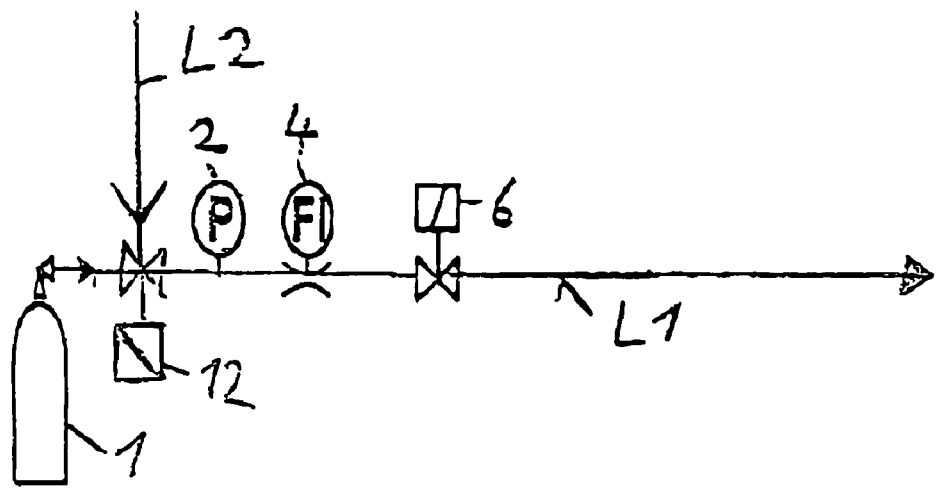

FIG. 5 shows another embodiment, whereby here no pressurized-gas source is employed for the other gas, but rather, the gas connection of the building or clinic itself, particularly for compressed air, is used. Thus, line L2 consists of a connection to the compressed-air system of the clinic. For the therapeutic treatment of the patient, the valve 12 is switched to communicate between the gas tank 1 and the valve 6. For purging purposes, the valve 12 is switched in such a way that the path to the gas tank 1 is closed. Compressed air from line L2 can then flow through the entire system, thus clearing line L1 all the way to the patient.

Figure 6:
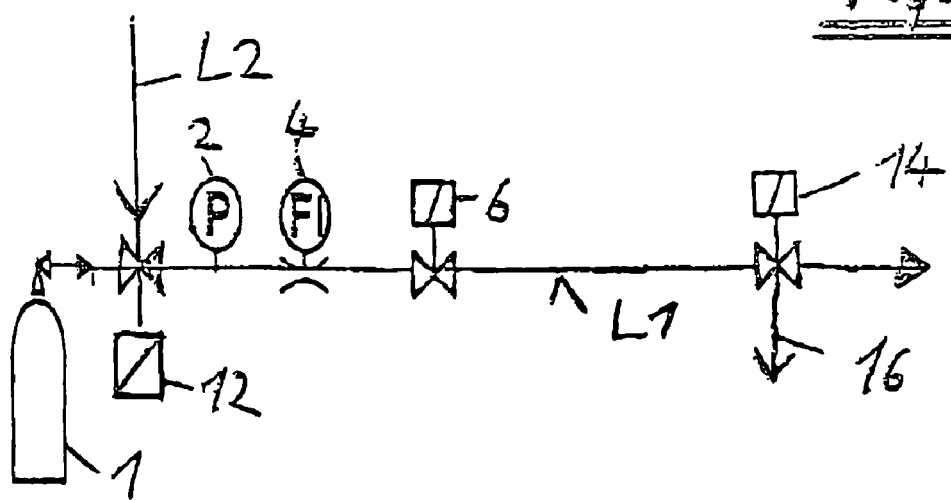

FIG. 6 shows another embodiment similar to the embodiment in FIG. 5. The difference here is a valve 14 which is located near the patient and by means of which a line 16 leading to the outside can be opened. The compressed air from line L2 can be passed through the entire system all the way to valve 14 shortly before the patient connection, thus removing harmful gas components from the line L1.

Figure 7:
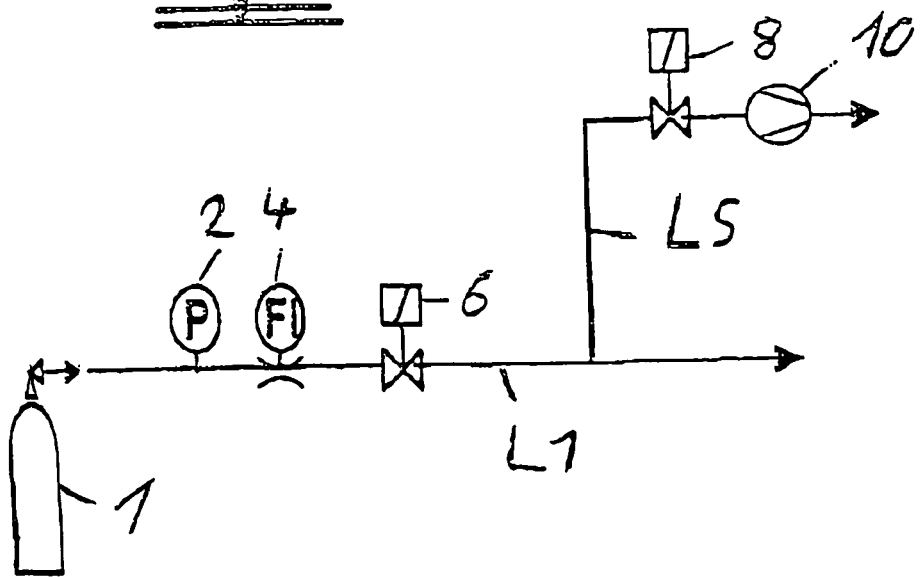
FIGS. 7 to 12 and 14: each depicting a device to carry out an evacuation operation according to the invention.

FIG. 7 shows another embodiment of the invention. The part of the first gas line L1 that leads from the gas reservoir tank 1 containing the therapeutic gas to the patient (lower arrow) is the same as in FIG. 1. The new aspect here is that an evacuation line LS is provided which comprises an evacuation line valve 8 and an evacuation element 10. This can be, for instance, a vacuum pump or else the vacuum connection at the hospital. If the patient is to be treated with the therapeutic gas after a treatment pause or prior to a new treatment, then, according to the invention, line L1 can be freed of gas residues by opening valve 8 and putting the vacuum pump 10 into operation. The vacuum pump 10 then evacuates the contaminated parts of the system. Once the evacuation line valve 8 is closed, the normal treatment modality can be resumed by opening valve 6.

Figure 8:
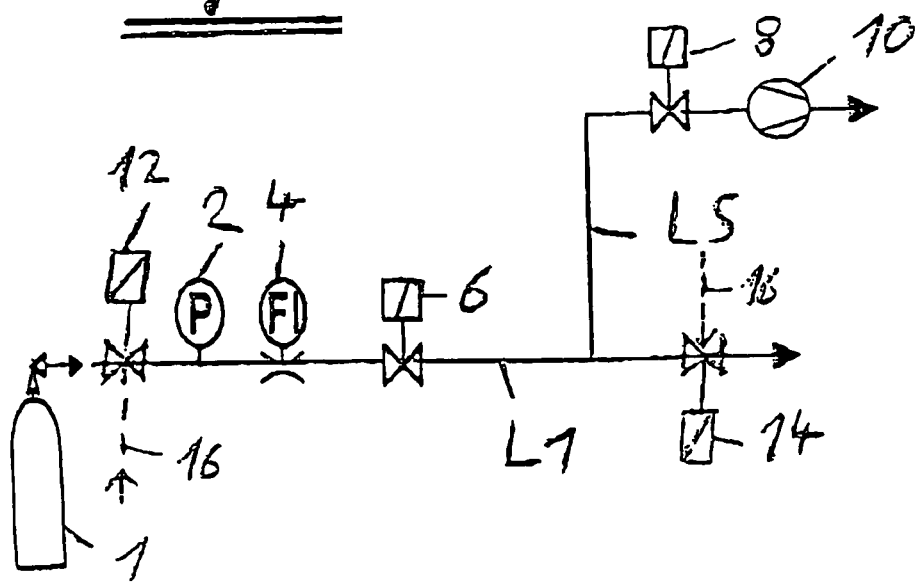

FIG. 8 shows another embodiment in which there is valve 12 near the gas tank 1 and there is a valve 14 near the patient. Once again, either only valve 12 can be employed or only valve 14, or else both valves. When the valves 12 and 14 are closed, L1 can be evacuated. Optionally, and thus drawn with a broken line, there can also be one or two lines 16 running from the outside to the valves 12 and 16 [sic]. During evacuation by means of the vacuum pump 10, opening the valve 12 causes an air current from the atmosphere to be drawn in and this air current can then enter the gas circulation system, for example, through the valve 12 or the valve 14. Thus, the line L1 is not only evacuated but also purged with atmospheric air. When one of the two valves 12 or 14 is closed, only the corresponding line 16 draws in air from the outside or from the patient device. When both valves are closed, the line L1 is evacuated.

Figure 9:
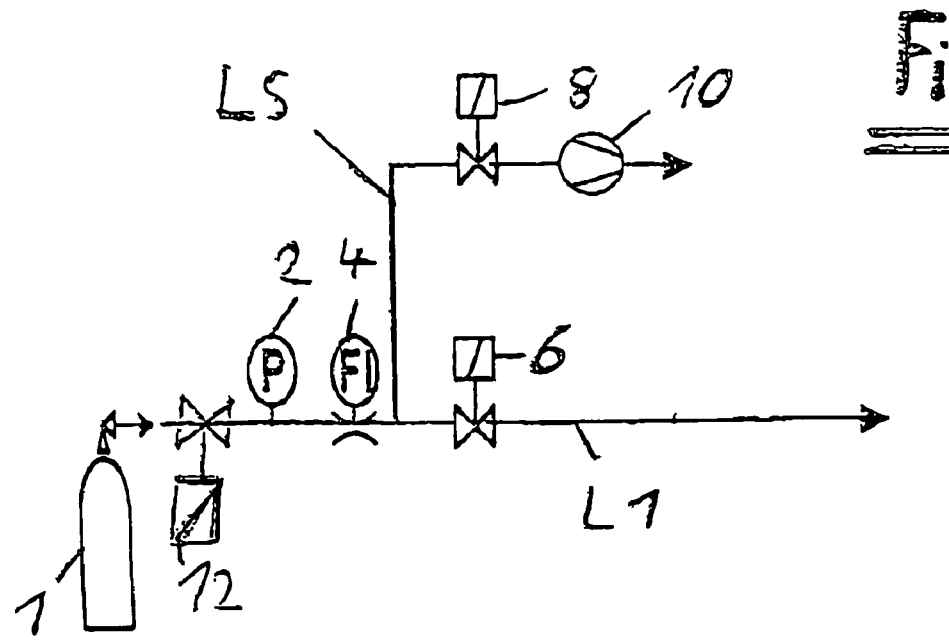

FIG. 9 shows another embodiment wherein the evacuation line LS is arranged at a different place. It is not located on the patient side of valve 6, but rather on the other side. In addition, the valve 12 is provided here, which allows the gas circulation system L1 to be shut off directly before the therapeutic gas tank 1, thus allowing an even larger area of the line L1 to be evacuated.

Figure 10:
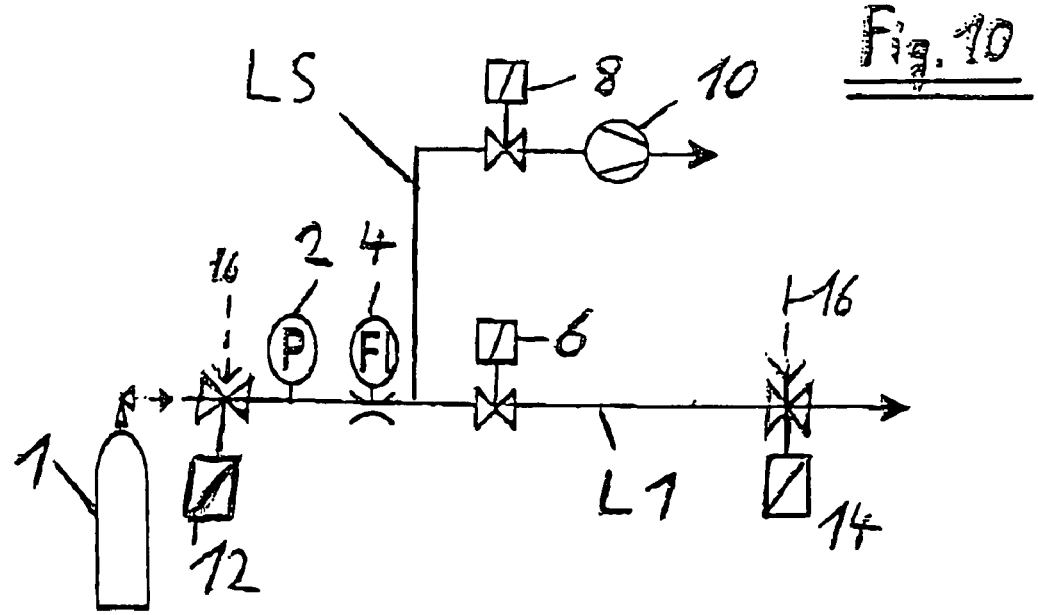

In FIG. 10, in addition to what is depicted in FIG. 9, the valve 14 is provided on the patient side, whereby here, it is optionally possible to provide an evacuation line 16 (hence drawn with a broken line). Then, during the evacuation operation, air can again enter line L1 via the evacuation line 16 and the valve 14. By the same token, the valve 12 can be provided with an evacuation line 16, by means of which this part of the system can also be vented.

Figure 11:
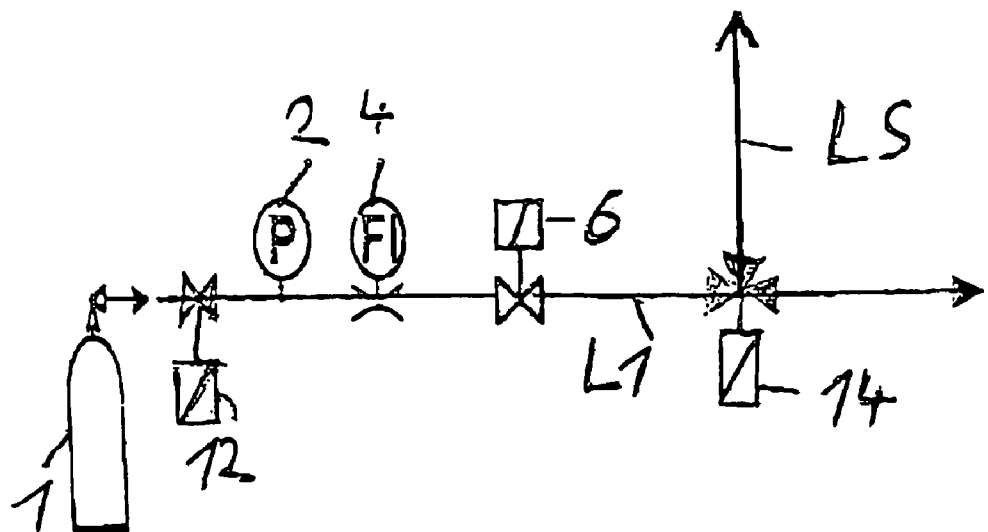

FIG. 11 shows another embodiment of the invention whereby the evacuation line LS is connected to L1 via a 3/2-way valve 14. Another valve 12 serves to separate the gas tank 1, thus allowing the purging of the line L1 in its entirety. A dedicated evacuation device or vacuum pump is not provided here but instead, the evacuation line LS is connected to the hospital's own negative-pressure network.

Figure 12:
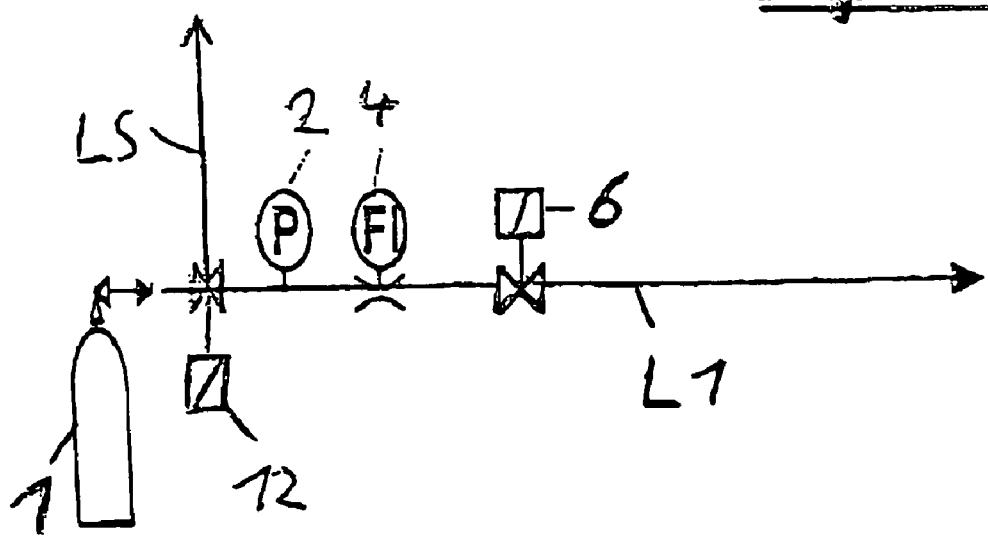

FIG. 12 shows a similar device except that the evacuation line connection LS is now directly near the gas tank 1 at the shut-off valve 12. In this manner as well, the line L1 can be cleared almost completely of detrimental gas components.

Figure 13:
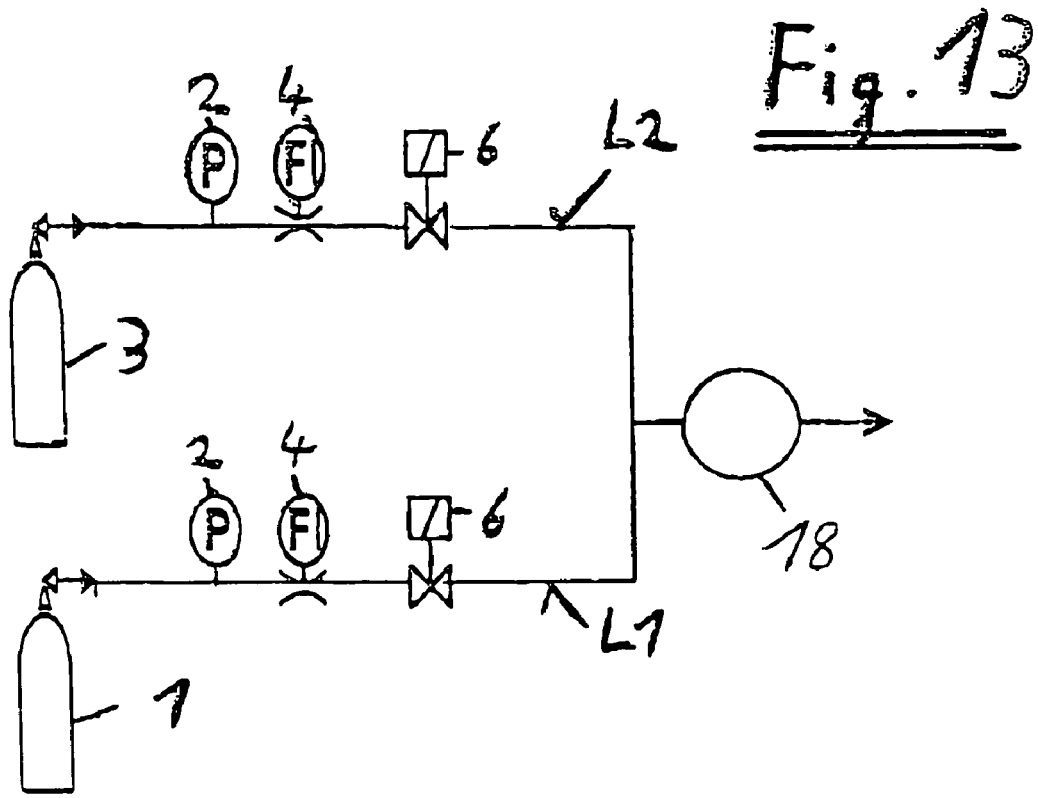

FIG. 13 corresponds essentially to FIG. 1. However, FIG. 13 additionally shows an aerosol atomizer 18 that can deliver one or more therapeutically effective substances to line L1. This atomizer can likewise be purged with purging gas from gas tank 3.

Such an aerosol atomizer 18 can also be employed, for example, in the embodiments shown in FIG. 2, 5 or 6. In FIG. 2, it is then preferably positioned before valve 16, whereby "before" means that the aerosol atomizer 18 is located upstream from the valve 16. In FIG. 5, it is preferably arranged before the patient, in FIG. 6 preferably between the valves 6 and 14.

Figure 14:
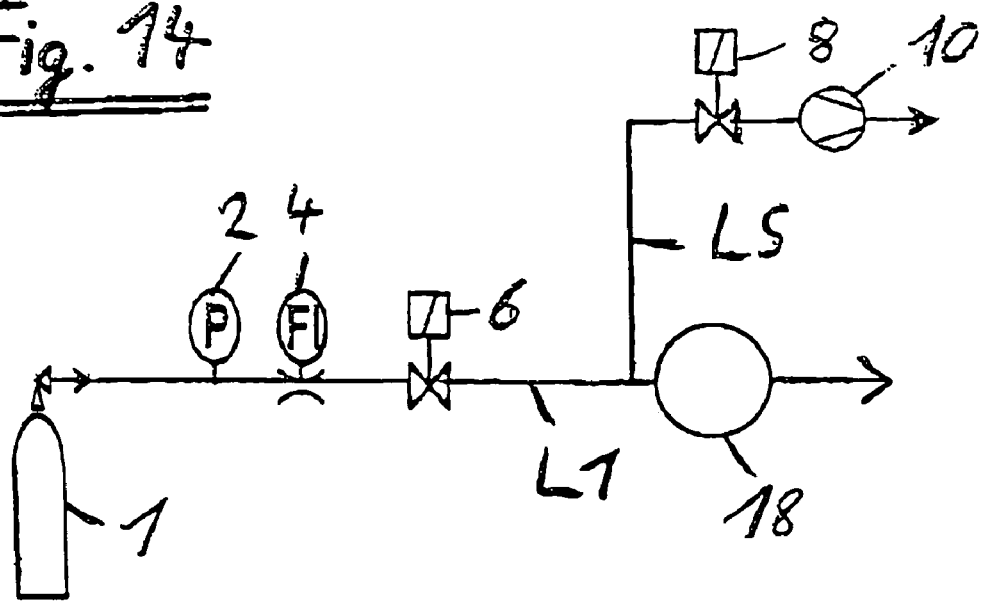

The embodiment shown in FIG. 14 corresponds essentially to the embodiment in FIG. 7. However, here an aerosol atomizer 18 is additionally provided which can deliver one or more therapeutically effective substances to line L1. This aerosol atomizer 18 likewise can be evacuated via the line LS.

Such an aerosol atomizer 18 can also be employed in the embodiments shown in FIGS. 8, 9 and 10. In FIG. 8, it would preferably be arranged before the valve 14, in FIG. 9 preferably before the patient and in FIG. 10 again before the valve 14.

What is claimed is:

1. A method for the metered administration of one or more therapeutically effective gases to a patient, comprising a step to remove harmful or undesired substances from the gas carrying system or from parts of the gas-carrying system, characterized in that the therapeutically effective gases are selected from the group consisting of NO, CO, $CO_2$ mixtures used to stimulate breathing, $H_2$ mixtures, $SF_6$ mixtures, and nitrosoethanol, the removal step comprising purging with at least one other gas or gas mixture selected from the group consisting of air, $O_2$, $N_2$, Ar, Xe, He, $SF_6$, mixtures thereof and other gases which do not have a therapeutic effect, supplying the one or more therapeutically effective gases from a gas source through a first line to the patient, providing at least one shut-off valve in the first line in selective flow communication with an outside line leading to the atmosphere, opening the shut-off valve to open flow communication with the outside line, and flowing the purge gas through the first line and out of the outside line to purge the first line.

2. The method according to claim 1, characterized in that the removal step is selected from the group consisting of one of time-controlled, sensor-controlled and event-controlled, and the parts of the system to be cleared comprise feed lines, valves, tubing, dead spaces, and patient intake elements.

3. The method according to claim 2, characterized in that the patient intake elements are selected from the group consisting of nosepieces and masks.

4. The method according to claim 1, characterized in that the removal step further comprises evacuation in addition to the purging.

5. The method according to claim 1, characterized in that the shut-off valve is provided at the first line upstream from a pressure gauge and a flow meter and a gas valve in the first line, and providing downstream from the pressure gauge and the flow meter and the gas valve of the first line a further shut-off valve having an outside line leading to the atmosphere.

6. The method according to claim 1, characterized in that two fo the shut-off valves are provided in the first line spaced from each other, and each of the shut-off valves having an outside line leading to the atmosphere.

7. A method for the metered administration of one or more therapeutically effective gases to a patient, comprising a step to remove harmful or undesired substances from the gas-carrying system or from parts of the gas-carrying system, characterized in that the therapeutically effective gases are selected from the group consisting of NO, CO, $CO_2$ mixtures used to stimulate breathing, $H_2$ mixtures, $SF_6$ mixtures, and nitrosoethanol, supplying the one or more therapeutically effective gases from a gas source through a first line to the patient, providing an evacuation line in flow communication with the first line, and evacuating the first line by applying suction to the evacuation line and thereby applying the suction to the first line for removing harmful or undesired substances from the first line.

8. The method according to claim 7, characterized in that the evacuation step is one of time-controlled, sensor-controlled and event-controlled, and the parts of the system to be cleared comprise feed lines, valves, tubing, dead spaces, and patient intake elements.

9. The method according to claim 7, characterized in that at least one shut-off valve is provided in the first line in selective flow communication with an outside line leading to the atmosphere, and opening the shut-off valve when the suction is applied to draw air into the outside line and to the first line to additionally purge the first line with air.

10. A device for the metered administration of one or more therapeutically effective gases to a patient, comprising a device to remove harmful or undesired substances, characterized by a therapeutic gas feed system including a first line feeding therapeutic gases selected from the group consisting of NO, CO, $CO_2$ mixtures used to stimulate breathing, $H_2$ mixtures, $SF_6$ mixtures, and nitrosoethanol, and the removal device including a second gas line in addition to the first gas line, the second gas line comprising purging structure for supplying a purging gas selected from the group consisting of $O_2$, $N_2$, Ar, Xe, He, $SF_6$, mixtures thereof and other gases which do not have a therapeutic effect, at least one shut-off valve in the first line, an outside line in flow communication with the outside valve, the outside line leading to the atmosphere, and the second line being in flow communication with the first line whereby upon opening the shut-off valve to open flow communication with the outside line purge gas may flow through the second line into the first line and into the outside line to the atmosphere.

11. The device according to claim 10, characterized in that the first gas line includes a pressure gauge, a flowmeter and a gas valve and in that the second line likewise includes a pressure gauge, a flowmeter and a valve.

12. The device according to claim 11, characterized in that there are two of the shut-off valves, each of the shut-off valves having an outside line leading to the atmosphere, one of the shut-off valves being upstream of the pressure gauge and the flowmeter and the gas valve of the first line, and the other of the shut-off valves being downstream of the pressure gauge and the flowmeter and the gas valve of the first line.

13. The device according to claim 10, characterized in that the second gas line is a compressed-air connection.

14. The device according to claim 10, characterized in that the removal device includes the evacuation line, and the evacuation line comprises one of an evacuation unit and a connection to an existing evacuation line.

15. The device according to claim 10, characterized in that there are two of the shut-off valves in the first line spaced from each other and each of which has an outside line leading to the atmosphere.

* * * * *